United States Patent [19]  [11] 4,241,064
Matsumura et al.  [45] Dec. 23, 1980

[54] 9H-PYRIDO[3,4-b]INDOLE DERIVATIVES

[75] Inventors: Shingo Matsumura, Kyoto; Hiroshi Enomoto, Nagaokakyo; Yoshiaki Aoyagi; Yoshitsugu Nomiyama, both of Kyoto; Tatsuhiko Kono, Suita; Masato Matsuda, Takatsuki; Haruo Tanaka, Hikone, all of Japan

[73] Assignee: Nippon Shinyaku Co. Ltd., Japan

[21] Appl. No.: 83,419

[22] Filed: Oct. 10, 1979

[30] Foreign Application Priority Data

Oct. 14, 1978 [JP] Japan ............................. 53-126352

[51] Int. Cl.$^3$ ................. C07D 471/04; A61K 31/395
[52] U.S. Cl. ...................................... 424/256; 546/85
[58] Field of Search ........................... 546/85; 424/256

[56] References Cited

PUBLICATIONS

Bradsher et al., "J. Org. Chem." vol. 28, No. 11, pp. 3070–3072 (1963).
Kump et al., "Helv. Chim. Acta" vol. 46, No. 2, pp. 498–505 (1963).

*Primary Examiner*—Alan L. Rotman
*Assistant Examiner*—Robert T. Bond
*Attorney, Agent, or Firm*—Jacobs & Jacobs

[57] ABSTRACT

1-Substituted-9H-pyrido[3,4-b]indole derivatives, which are further optionally substituted in the 3- or 4-position, are inhibitors of xanthine-oxidase. A representative embodiment is 1-formyl-4-hydroxy-9H-pyrido[3,4-b]indole which can be prepared through the processing of *Picrasma quassioides*.

14 Claims, No Drawings

9H-PYRIDO[3,4-B]INDOLE DERIVATIVES

The present invention pertains to 1-substituted-9H-pyrido[3,4-b]indole derivatives. Specifically the invention pertains to 9H-pyrido[3,4-b]indoles of the formula:

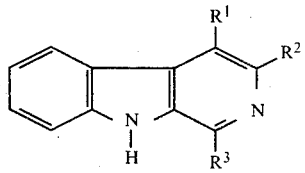

wherein
one of $R^1$ and $R^2$ is hydrogen and the other is hydrogen, hydroxy or $-OR^4$ wherein $R^4$ is alkanoyl of 2 to 7 carbon atoms, tosyl or mesyl, and $R^3$ is hydroxymethyl, formyl, carboxy or carbalkoxy wherein alkoxy contains 1 to 6 carbon atoms.

By the term alkanoyl of 2 to 7 carbon atoms is intended a group of the formula $(C_xH_{2x+1})CO$ wherein x has a value of 1 to 6 as for example acetyl, propionyl, butyryl and the like. Alkoxy of 1 to 6 carbon atoms refers to the group $(C_xH_{2x+1})-O-$ wherein x is as defined above.

The foregoing compounds have the property of inhibiting the enzyme xanthine-oxidase. As is known, xanthine-oxidase inhibitors improve hyperuricacidemia by suppressing the formation of uric acid and, as such, find use as therapeutic and prophylactic agents in the treatment of gout, calculus in the urinary organ, tissue degeneration of the circulatory system, and the like. The xanthine-oxidase inhibitory activity is expressed in terms of the concentration of the agent at which a 50% inhibition of xanthine-oxidase activity is observed ($IC_{50}$). This can be readily measured pre-incubation of test specimens at varying concentrations in phosphate buffer (pH 7.5) for 5 minutes, then adding 10 μM of xanthine, measuring the enzyme activity (Kalker), and comparing the assay result with the activity of a control to determine the percent inhibition. (The $IC_{50}$ value being derived from a plot of concentration versus percent inhibition).

Typical $IC_{50}$ values for compounds of the present invention are as follows:

TABLE I

| $R^1$ | $R^2$ | $R^3$ | $IC_{50}$ |
|---|---|---|---|
| OH | H | CHO | $6.5 \times 10^{-4}$ |
| OCOCH$_3$ | H | CHO | $1.7 \times 10^{-3}$ |
| OH | H | CH$_2$OH | $7.2 \times 10^{-2}$ |
| OH | H | COOH | $2.5 \times 10^{-1}$ |
| H | OH | CHO | $3.8 \times 10^{-1}$ |
| H | H | CHO | $8 \times 10^{-1}$ |
| H | H | CH$_2$OH | 4.3 |
| OH | H | COOCH$_3$ | 19 |
| H | H | COOCH$_3$ | 40 |

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In addition, significant potentiation of the antitumor activity of mitomycin C and similar antibiotics can be observed in conventional laboratory models. Thus, ddY mice (male, body weights ca 18 g) were reared for a week and $1 \times 10^6$ Ehrlich ascites cells/animal were intraperitoneally transplanted. After 24 hours, mitomycin C or/and compound 1 were administered intraperitoneally for 7 consecutive days. The mice were divided in 4 groups of 10 animals each: a first group received 0.5 mg/kg/day of mitomycin C; a second group received 50 mg/kg/day of compound 1 (1-formyl-4-hydroxy-9H-pyrido[3,4-b]indole); a third group received 0.5 mg/kg/day of mitomycin C plus 50 mg/kg/day of compound 1; and a control group given 0.5% carboxymethyl-cellulose. The results are as follows:

TABLE II

| | Survival Rate (%) | | | |
|---|---|---|---|---|
| Day | Control | Compound 1 | Mitomycin | Compound 1 + Mitomycin |
| 16 | 100 | 100 | 100 | 100 |
| 17 | 100 | 90 | 100 | 100 |
| 18 | 90 | 80 | 100 | 100 |
| 19 | 80 | 80 | 100 | 100 |
| 20 | 70 | 70 | 100 | 100 |
| 21 | 70 | 70 | 100 | 100 |
| 22 | 50 | 40 | 90 | 100 |
| 23 | 40 | 30 | 90 | 100 |
| 24 | 10 | 10 | 90 | 100 |
| 25 | — | 10 | 90 | 100 |
| 26 | — | 10 | 90 | 100 |
| 27 | — | — | 90 | 100 |
| 28 | — | — | 80 | 100 |
| 29 | — | — | 70 | 100 |
| 30 | — | — | 70 | 100 |
| * | — | — | * | * |
| 33 | — | — | 70 | 100 |
| 34 | — | — | 60 | 100 |
| * | — | — | * | * |
| 38 | — | — | 60 | 100 |
| 39 | — | — | 50 | 100 |
| * | — | — | * | * |
| 48 | — | — | 50 | 100 |
| 49 | — | — | 40 | 90 |
| * | — | — | * | * |
| 52 | — | — | 40 | 90 |
| 53 | — | — | 30 | 90 |
| * | — | — | * | * |
| 56 | — | — | 30 | 90 |
| 57 | — | — | 20 | 90 |
| 58 | — | — | 20 | 90 |
| 59 | — | — | 20 | 90 |
| 60 | — | — | 20 | 90 |

*No change during interval.

The results showed that all animals in the control group died between day 18 through day 24 and all the animals in the group dosed with compound 1 alone died between day 17 through day 27. The survival rate for the group given mitomycin C alone was 20%, 60 days after transplantation. In the group dosed with both mitomycin C and compound 1, however the survival rate was 90%, 60 days after transplantation.

A single intraperitoneal administration of 1 mg/kg of mitomycin C and 50 mg/kg of compound 1 at day 6 after transplantation resulted also in an increase in survival rate as compared with the group receiving a single intraperitoneal administration of 1 mg/kg of mitomycin C, as can be seen from Table III.

TABLE III

| | No. Surviving | | |
|---|---|---|---|
| Day | Control | Mitomycin | Compound 1 + Mitomycin |
| 10 | 7 | 7 | 7 |
| 11 | 7 | 7 | 7 |
| 12 | 6 | 7 | 7 |
| 13 | 6 | 7 | 7 |
| 14 | 6 | 7 | 7 |
| 15 | 6 | 7 | 7 |
| 16 | 5 | 7 | 7 |
| 17 | 5 | 7 | 7 |
| 18 | 5 | 5 | 7 |
| 19 | 2 | 5 | 7 |
| 20 | 2 | 4 | 6 |
| 21 | 1 | 4 | 5 |
| 22 | — | 4 | 5 |
| 23 | — | 2 | 5 |
| 24 | — | 2 | 5 |
| 25 | — | 1 | 5 |
| 26 | — | 1 | 5 |
| 27 | — | 1 | 5 |
| 28 | — | 1 | 5 |
| 29 | 1 | — | 4 |
| 30 | — | — | 3 |
| 31 | — | — | 3 |
| 32 | — | — | 3 |
| 33 | — | — | 2 |
| 34 | — | — | 2 |
| * | — | — | * |
| 40 | — | — | 2 |

*No change during interval.

These compounds can be obtained by the proper processing of material from natural sources and by chemical modifications described hereinafter in greater detail. In particular, the compound 1-formyl-4-hydroxy-9H-pyrido[3,4-b]indole and the corresponding 1-carbomethoxy compound can be obtained from *Picrasma quassioides* Benn.

*Picrasma quassioides* Benn., known in Chinese medicine as "picrasma wood", has been used for the production of picrasma extract and picrasma tincture which are bitter stomachics. [Tatsuo Kariyone & Yushiro Kimura, Yakuyo Shokubutsu Dai-Jiten (Hirokawa Shoten), 262 (1963)]. Two components, quassiin and nigakinone, have been identified in this herb medicine, but are unrelated chemically or pharmacologically to the present compounds.

According to the present invention, commercial picrasma wood, dry pulverized picrasma wood or, preferably, the dry pulverized powder of its heart wood, is extracted with a polar organic solvent such as water or methanol and the extract is then concentrated to yield a whole picrasma extract. This extract is then fractionated as for example by Sephadex LH or silica gel chromatography. The fractions are assayed for xanthine-oxidase inhibitory activity and the active fraction this then purified as by recrystallization.

In this fashion there is obtained 1-formyl-4-hydroxy-9H-pyrido[3,4-b]indole and 1-carbomethoxy-4-hydroxy-9H-pyrido-[3,4-b]indole.

1-Formyl-4-hydroxy-9H-pyrido[3,4-b]indole can also be obtained by reduction of 1-carbomethoxy-4-hydroxy-9H-pyrido-[3,4-b]indole, optionally with protection of the hydroxy group, as for example with diisobutyl aluminum hydride (DIBAL).

3-Hydroxy compounds can be obtained through formation of the N-oxide followed by reduction.

Thus 1-carbomethoxy-9H-pyrido[3,4-b]indole is N-oxidized with a peracid such as m-chloroperbenzoic acid and subjected to a rearrangement treatment to obtain the 3-acetoxy compound which is then reduced with DIBAL to obtain 1-formyl-3-hydroxy-9H-pyrido[3,4-b]indole.

Formation of the 3- and 4-esters (—OR$^4$) is achieved through conventional esterification techniques. Formation of the compounds wherein R$^3$ is hydroxymethyl are obtained by reduction of the formyl derivatives. Compounds in which R$^3$ is carboxy are obtained by conventional oxidation which can be followed by conventional esterification with lower alkanol derivatives wherein R$^3$ is carbalkoxy.

The following examples will serve to further typify the nature of the invention but should not be construed as a limitation on the scope thereof which is defined solely by the appended claims.

EXAMPLE 1

1-Formyl-4-Hydroxy-9H-Pyrido[3,4-b]Indole

Commercial dry pulverized picrasma wood (10 kg) was extracted with 25 l of methanol at room temperature overnight. This procedure was repeated three times and the extracts were pooled and concentrated to obtain 170 g of tannish-brown powdery extract. The xanthine-oxidase inhibitory activity of this extract was $KC_{50}=5$ γ/ml. Two grams of this extract were fractionated on 200 g of Sephadix LH-20, the chromatogram being developed with methanol. The eluate was collected in 14 ml fractions. Fraction Nos. 41 through 45 were pooled and concentrated to obtain 30 mg of a fraction showing an activity of $IC_{50}=0.1$ γ/ml. This fraction was dissolved in 30 ml of methanol and fractionated by high performance liquid chromatography (Waters Model 440). Bondapak C$_{18}$ (reverse-phase) was used as the packing material and 1:1 methanol:water was used as the developing solvent. With 2 ml per injection, elution was carried out at the rate of 6 ml per minute. The activity was detected at 6 to 10 minutes. This fractionation was repeated to obtain 5 mg of a fraction with $IC_{50}=0.02$ γ/ml. This fraction was further fractionated on analytical packing material, μ-Bondapak C$_{18}$, and developed with a 1:1 methanol:water at the rate of 2 ml per minute. At 6 minutes after injection, substance [I] emerged as a single peak. The above procedure was then repeated with injection doses of 100 μl, to yield from 170 g of extract, 17 mg of 1-formyl-3-hydroxy-9H-pyrido[3,4-b]indole. (Yield based on extract: 0.01%). Recrystallization from water-methanol yields pale-yellow needles melting at 296°–298° C. (decomp.). This substance produces an orange color with 2,4-dinitrophenylhydrazine. High resolution mass spectrum: M$^+$=212.0644, corresponding to a molecular formula of C$_{12}$H$_8$N$_2$O$_2$ (212.058573). The above crystalline product was dissolved in ethanol and an UV absorption spectrum was measured. The UV spectrum shows absorption maxima at 370, 283, 240 and 210 mμ. On the alkaline side, the spectrum showed increased intensities of absorption at 370 and 283 mμ. These absorptions indicate the existence of a β-carboline nucleus. In the infrared region of the spectrum, absorptions at 3350, 1660 and 1610 cm$^{-1}$ indicate the existence of NH, CHO and OH groups. NMR(in DMSO-d$_6$): δ11.90 ppm (NH), 10.11 ppm (CHO), 8.21 ppm (3-H), 7.58, 7.65, 7.90 and 8.33 ppm (4-benzene-ring protons), 7.58–8.0 ppm (OH).

EXAMPLE 2

1-Carbomethoxy-4-Hydroxy-9H-Pyrido[3,4-b]Indole

Twenty grams of picrasma wood extract were fractionated on 2.0 kg of Sephadex LH-20 and elution was carried out with methanol, the eluate being collected in 100 ml fractions. Fraction Nos. 11 through 21 yielded 1.50 g of nigakinone, while fraction Nos. 22 through 38 yielded 0.12 g of crystals. The yield of the latter was 0.6% based on the extract. Recrystallization from dioxane yielded 1-carbomethoxy-4-hydroxy-9H-pyrido[3,4-b]indole as colorless prisms melting at 241°–242° C.

IR spectrum: 3400, 2600–3100, 1670 and 1610 cm$^{-1}$. UV spectrum (ethanol): absorption maxima at 365, 350, 304 and 280 mμ. Elemental analysis found: C, 64.62%; H, 3.77%; N, 11.58%; calculated for C$_{13}$H$_{10}$N$_2$O$_3$ (mol. wt. 242): C, 64.46%; H, 4.16%; N, 11.57%. Mol. wt. (based on mass spectrum) 242. NMR (DMSO-d$_6$): δ4.0 ppm, 3H (COOCH$_3$), 11.45 ppm, 1H (NH), 8.0–8.4 ppm, 2H, 10.0 ppm, 1H (OH), 7.2–7.8 ppm, 3H.

EXAMPLE 3A

1-Carbomethoxy-4-Acetoxy-9H-Pyrido[3,4-b]Indole

Four grams of 1-carbomethoxy-4-hydroxy-9H-pyrido[3,4-b]-indole were dissolved in a mixture of 20 ml pyridine and 24 ml acetic anhydride and the solution was allowed to stand at room temperature overnight. The resultant crystals were collected by filtration and recrystallized from methanol to yield 2.9 g of the title compound. Yield 61.8% colorless prisms, m.p. 220°–221° C. Elemental analysis—found: C, 63.23%; H, 3.94%, N, 9.59%; calculated for C$_{15}$H$_{12}$N$_2$O$_4$ (mol. wt. 284): C, 63.38%; H, 4.26%; N, 9.86%. Mol. wt. (based on mass spectrum) 284. NMR (DMSO-d$_6$): δ2.62 ppm, 3H (COCH$_3$), 4.07 ppm, 3H (COOCH$_3$), 8.37 ppm, 1H (3-H), 7.20–8.20 ppm, 4H, 11.85 ppm; 1H (NH). UV spectrum (methanol): 360, 300, 264, 243, 212 mμ. IR spectrum: 3380, 1760, 1675, 1242, 1222 cm$^{-1}$.

EXAMPLE 3B

1-Formyl-4-Hydroxy-9H-Pyrido[3,4-b]Indole

In 70 ml of dry tetrahydrofuran were dissolved 540 mg of the product obtained in Example 3A and cooled in a dry ice-acetone bath. Seven milliliters of di-isobutyl-aluminum hydride were added. After 2 hours, the reaction mixture was rendered alkaline with ammonia and the precipitated reagent was filtered off, the solvent removed by distillation, and the residue crystallized from methanol-water. Thus obtained were 140 mg of pale-yellow needles, m.p. 296°–298° C., identical with the product of Example 1 in IR, UV, NMR and mass spectrum. Mixed melting caused no melting point depression.

EXAMPLE 4

1-Carbomethoxy-4-Tosyloxy-9H-Pyrido[3,4-b]Indole

In 10 ml of dioxane were dissolved 24.2 mg of the product of Example 2, followed by addition of 19.0 mg of p-toluenesulfonyl chloride and 10 mg of sodium carbonate. The mixture was stirred at room temperature for 4 hours and the resultant crystals were recovered by filtration and recrystallized from methanol to yield 35 mg of the title compound as colorless needles, m.p. 230°–231° C. Yield 89.7%.

EXAMPLE 5

1-Carbomethoxy-9H-Pyrido[3,4-b]Indole-2-N-Oxide

In 150 ml of chloroform were dissolved 3.7 g of 1-carbomethoxy-9H-pyrido[3,4-b]indole, followed by the addition of 13.8 g of m-chloroperbenzoic acid. The mixture was stirred at room temperature for 16 hours, at the end of which time it was extracted with 5% sodium bicarbonate solution and washed with water. The chloroform layer was concentrated to yield 800 mg of the title N-oxide, yield 20.2%, which was recrystallized from ethyl acetate-methanol to yield crystals melting at 192°–193° C.

EXAMPLE 6

1-Carbomethoxy-3-Acetoxy-9H-Pyrido[3,4-b]Indole

The N-oxide prepared in Example 5 (24.2 mg) was dissolved in 3 ml of acetic anhydride and the solution allowed to stand at 80° C. (water bath) for 2 hours. The reaction mixture was then poured into water, the solvent removed by distillation, and the residue recrystallized from isopropanol-water to yield 15 mg of the title compound as yellow needles, m.p. 151°–152° C. Yield 52.82%. NMR (DMSO-d$_6$): 3.99 ppm, 3H (COOC$\underline{H}_3$), 2.33 ppm, 3H (COC$\underline{H}_3$), 8.16 ppm, 1H (4-H), 8.22 ppm, 1H, 7.2–7.8 ppm, 3H. Mol. wt. (based on mass spectrum) 284. IR absorption spectrum: 3400, 1750, 1690, 1622, 1222 cm$^{-1}$. UV absorption spectrum (methanol): 375, 300, 275, 265, 258, 242 mμ. The solution assumed a yellowish color on being rendered alkaline.

EXAMPLE 7

1-Formyl-3-Hydroxy-9H-Pyrido[3,4-b]Indole

In 50 ml of dry tetrahydrofuran were dissolved 135 mg of the product of Example 6, followed by addition of 2 ml of di-isobutyl-aluminum hydride. The reaction mixture was allowed to stand with dry ice-acetone cooling for 2 hours and then poured into water. The precipitated reagent was removed, the solvent removed by distillation and the residue recrystallized from water-methanol to yield 10 mg of the title compound melting at 290°–295° C. (decomp.). Mol. wt. (based on mass spectrum) 212. IR absorption spectrum: 3300, 1640, 1620, 1600 cm$^{-1}$. UV absorption spectrum (MeOH): 420, 292, 282, 262 mμ. NMR spectrum (DMSO-d$_6$): 10.1 ppm, 1H (CHO), 7.7 ppm, 1H (4-H), 8.2 ppm, 1H, 7.2–7.6 ppm, 3H.

EXAMPLE 8

1-Formyl-4-Acetoxy-9H-Pyrido[3,4-b]Indole

The product of Example 1 (51 mg) was stirred with 1.0 ml of acetic anhydride and 0.5 ml of pyridine at room temperature for 2 hours, and the resultant white precipitate was collected by filtration and recrystallized from methanol, to yield 12 mg of colorless needles melting at 250°–252° C. (decomp.). IR absorption spectrum: 3370 (HN), 1760 (COCH$_3$), 1680 (CHO) cm$^{-1}$. Mol. wt. (based on mass spectrum) 254.

EXAMPLE 9

1-Hydroxymethyl-9H-Pyrido[3,4-b]Indole

In 50 ml of dry tetrahydrofuran were dissolved 160 mg of 1-carbomethoxy-9H-pyrido[3,4-b]indole. The solution was cooled with ice, 2 ml of diisobutyl-aluminum hydride were added and the reaction mixture allowed to stand for 2 hours. Unreacted reagent was then decomposed with a small amount of water and the mixture extracted with chloroform. The chloroform was removed by distillation and the residue recrystallized from methanol to yield 30 mg of 1-hydroxymethyl-9H-pyrido[3,4-b]indole as pale-yellow needles melting at 228°–230° C. The IR spectrum shows the absorption peak at 1680 cm$^{-1}$ has disappeared, with an intense absorption being observed at 1630 cm$^{-1}$. Mol. wt. (based on mass spectrum) 198.

EXAMPLE 10

1-Hydroxymethyl-4-Hydroxy-9H-pyrido[3,4-b]Indole

In 30 ml of dry tetrahydrofuran were dissolved 70 mg of the product of 1-carbomethoxy-4-acetoxy-9H-pyrido[3,4-b]indole. With ice-cooling, 4.0 ml of diisobutylaluminum hydride were added. The reaction mixture was allowed to stand for 2 hours, after which the unreacted reagent was decomposed with a small amount of water. The mixture was then extracted with ethyl acetate. The organic layers were pooled and concentrated and the resultant crystals were recrystallized from ethyl acetate to yield 16 mg of the title compound as white needles melting at 148°–150°0 C. (decomp.). The IR absorption spectrum shows absorption at 1680 cm$^{-1}$ has disappeared. An intense absorption was observed at 1620 cm$^{-1}$. Mol. wt. (based on mass spectrum) 214.

EXAMPLE 11

1-Carboxy-9H-Pyrido[3,4-b]Indole

In 30 ml of methanol was dissolved 0.5 g of 1-carbomethoxy-9H-pyrido[3,4-b]indole and to this solution was added 2 ml of 10% aqueous sodium hydroxide. The mixture was refluxed at water bath temperature for 6 hours, the methanol removed by distillation, the residue neutralized with 10% hydrochloric acid and the resultant crystals recovered by filtration. Recrystallization from methanol yields 350 mg of 1-carboxy-9H-pyrido[3,4-b]indole as colorless needles, m.p. 239°–240° C. (decomp.). Mol. wt. (based on mass spectrum) 212. The IR absorption spectrum shows absorption at 1680 cm$^{-1}$ in the starting compound has disappeared and, instead, an absorption of the carboxyl group is observed at 1580–1600 cm$^{-1}$.

EXAMPLE 12

1-Carboxy-4-Hydroxy-9H-Pyrido[3,4-b]Indole

In 30 ml of methanol was dissolved 1.0 g of the product of Example 2 followed by addition of 2 ml of 10% aqueous sodium hydroxide. The mixture was refluxed at water bath temperature for 6 hours and the methanol then removed by distillation. The residue was neutralized with a 10% aqueous hydrochloric acid and the resultant crystals were recovered by filtration and recrystallized from methanoltetrahydrofuran to yield 630 mg of the title compound as colorless needles, m.p. 158°–159° C. (decomp.). Mol. wt. (based on mass spectrum) 228. Elemental analysis found: C, 63.32%; H, 3.28%; N, 12.05%; calculated for C$_{12}$H$_8$N$_2$O$_3$: C, 63.16%; H, 3.53%; N, 12.28%. The IR absorption spectrum shows the absorption at 1680 cm$^{-1}$ in starting compound has disappeared with absorption observed at 1610 cm$^{-1}$ (carbonyl).

What is claimed is:

1. A compound of the formula:

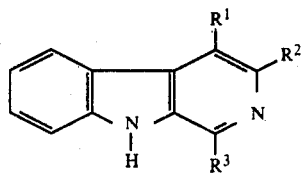

wherein
one of $R^1$ and $R^2$ is hydrogen and the other is hydroxy or —$OR^4$ wherein $R^4$ is alkanoyl of 2 to 7 carbon atoms, tosyl or mesyl, and
$R^3$ is hydroxymethyl, formyl, carboxy or carbalkoxy wherein alkoxy contains 1 to 6 carbon atoms.

2. A compound according to claim 1 wherein $R^1$ is hydrogen.

3. A compound according to claim 1 wherein $R^1$ is hydrogen or —$OR^4$ in which $R^4$ is as therein defined, and $R^2$ is hydrogen.

4. A compound according to claim 1 wherein $R^1$ is hydroxy and $R^3$ is carbalkoxy.

5. The compound according to claim 1 which is 1-formyl-4-hydroxy-9H-pyrido[3,4-b]indole.

6. The compound according to claim 1 which is 1-carbomethoxy-4-hydroxy-9H-pyrido[3,4-b]indole.

7. The compound according to claim 1 which is 1-formyl-3-hydroxy-9H-pyrido[3,4-b]indole.

8. The compound according to claim 1 which is 1-formyl-4-acetoxy-9H-pyrido[3,4-b]indole.

9. The compound according to claim 1 which is 1-hydroxymethyl-4-hydroxy-9H-pyrido[3,4-b]indole.

10. The compound according to claim 1 which is 1-carboxy-4-hydroxy-9H-pyrido[3,4-b]indole.

11. The compound according to claim 1 which is 1-carbomethoxy-4-acetoxy-9H-pyrido[3,4-b]indole.

12. The compound according to claim 1 which is 1-carbomethoxy-4-tosyloxy-9H-pyrido[3,4-b]indole.

13. The compound according to claim 1 which is 1-carbomethoxy-3-acetoxy-9-pyrido[3,4-b]indole.

14. The method of inhibiting uric acid formation in humans and other animals through inhibition of xanthine oxidase which comprises administering thereto an effective amount of a compound of the formula:

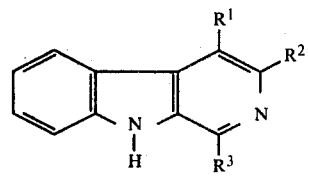

wherein
one of $R^1$ and $R^2$ is hydrogen and the other is hydrogen, hydroxy or —$OR^4$ wherein $R^4$ is alkanoyl of 2 to 7 carbon atoms, tosyl or mesyl, and
$R^3$ is hydroxymethyl, formyl, carboxy or carbalkoxy wherein alkoxy contains 1 to 6 carbon atoms.

* * * * *